United States Patent
Kaizik et al.

(10) Patent No.: US 8,455,701 B2
(45) Date of Patent: Jun. 4, 2013

(54) METHOD FOR PRODUCING DECANOLS BY MEANS OF HYDROGENATING DECENALS

(75) Inventors: Alfred Kaizik, Marl (DE); Hans-Gerd Lueken, Marl (DE)

(73) Assignee: Evonik Oxeno GmbH, Marl (DE)

( * ) Notice: Subject to any disclaimer, the term of this patent is extended or adjusted under 35 U.S.C. 154(b) by 0 days.

(21) Appl. No.: 13/502,226

(22) PCT Filed: Aug. 13, 2010

(86) PCT No.: PCT/EP2010/061827
§ 371 (c)(1),
(2), (4) Date: May 30, 2012

(87) PCT Pub. No.: WO2011/045102
PCT Pub. Date: Apr. 21, 2011

(65) Prior Publication Data
US 2012/0253083 A1     Oct. 4, 2012

(30) Foreign Application Priority Data

Oct. 15, 2009   (DE) .......................... 10 2009 045 718

(51) Int. Cl.
*C07C 29/14* (2006.01)
(52) U.S. Cl.
USPC ........................................................ 568/881
(58) Field of Classification Search
USPC ........................................................ 568/881
See application file for complete search history.

(56) References Cited

U.S. PATENT DOCUMENTS

| 5,093,534 | A  | 3/1992  | Ludwig et al. |
| 6,680,414 | B2 | 1/2004  | Knoop et al. |
| 7,138,552 | B2 | 11/2006 | Kaizik et al. |
| 7,361,714 | B2 | 4/2008  | Grass et al. |
| 7,524,997 | B2 | 4/2009  | Kaizik et al. |
| 2006/0041167 | A1 | 2/2006 | Grass et al. |
| 2006/0161017 | A1 | 7/2006 | Grass et al. |
| 2011/0060169 | A1 | 3/2011 | Kaizik et al. |

FOREIGN PATENT DOCUMENTS

| DE | 10 2007 041 380 | 3/2009 |
| EP | 0 470 344 | 2/1992 |
| GB | 1 244 442 | 9/1971 |
| WO | 03 095402 | 11/2003 |

OTHER PUBLICATIONS

International Search Report Issued Mar. 10, 2011 in PCT/EP10/61827 Filed Aug. 13, 2010.
U.S. Appl. No. 13/502,226, filed Apr. 16, 2012, Kaizik, et al.
U.S. Appl. No. 11/320,409, filed Dec. 29, 2005, Grass, et al.
U.S. Appl. No. 12/674,910, filed Feb. 24, 2010, Kaizik, et al.
U.S. Appl. No. 13/256,116, filed Sep. 27, 2011, Kaizik, et al.
U.S. Appl. No. 13/498,690, filed Mar. 28, 2012, Kaizik, et al.
U.S. Appl. No. 13/381,735, filed Feb. 16, 2012, Lueken, et al.
U.S. Appl. No. 10/519,413, filed Jan. 6, 2005, Grass, et al.

*Primary Examiner* — Elvis O Price
(74) *Attorney, Agent, or Firm* — Oblon, Spivak, McClelland, Maier & Neustadt, L.L.P.

(57) ABSTRACT

The present invention relates to a method for producing at least one decanol by means of hydrogenating at least one decenal, wherein a first hydrogenation is carried out in the liquid phase on a solid first catalyst, wherein the first catalyst contains copper and nickel. The aim of the invention is to provide a method of the type mentioned above, according to which decenals can be hydrogenated into decanols in high yields even after long operating periods. The content of non-reacted decenals in the hydrogenation discharge in particular should be less than 1500 ppm. Said aim is achieved by carrying out the hydrogenation in two steps, which is to say in a first step in a known manner using a catalyst comprising copper, nickel and optionally chromium and/or barium oxide, and subsequently in a second step using a different catalyst that must be free of copper, chromium and nickel.

10 Claims, No Drawings

METHOD FOR PRODUCING DECANOLS BY MEANS OF HYDROGENATING DECENALS

The present invention relates to a process for preparing at least one decanol by hydrogenation of at least one decenal, in which a first hydrogenation is effected in the liquid phase over a solid first catalyst, said first catalyst comprising copper and nickel.

Such a process is known from DE102007041380A1.

Decanols in the context of this invention are saturated alcohols having ten carbon atoms. Representatives of the group of the decanols are: 2-propylheptanol, 4-methyl-2-propylhexanol, 5-methyl-2-propylhexanol, 2-isopropyl-4-methylhexanol, 2-isopropyl-5-methylhexanol, each of the decanols listed consisting of at least two stereoisomers.

Decanols serve as precursors for the production of plasticizers and as intermediates for the production of detergents.

Decenals in the context of this invention are $\alpha,\beta$-unsaturated aldehydes having ten carbon atoms. They are obtained especially by aldolization of the saturated $C_5$-aldehydes (pentals). Representatives of the group of the decenals are: 2-propyl-heptenal, 4-methyl-2-propylhexenal, 5-methyl-2-propylhexenal, 2-isopropyl-4-methylhexenal, 2-isopropyl-5-methylhexenal.

It is known that carbonyl compounds, especially aldehydes, can be reduced catalytically with hydrogen to alcohols. The catalysts used frequently contain at least one metal from groups 1b, 2b, 6b, 7b and/or 8 of the periodic table of the elements. The hydrogenation of aldehydes can be performed continuously or batchwise with catalyst powders or lumps in the gas or liquid phase.

For the industrial preparation of alcohols by hydrogenation of aldehydes from the oxo process (hydroformylation of olefins) or from aldol condensation of aldehydes, particularly in the case of large products, continuous processes with fixed bed catalysts in the gas or liquid phase are employed.

Compared to gas phase hydrogenation, liquid phase hydrogenation has the more favorable energy balance and the higher space-time yield. With rising molar mass of the aldehyde to be hydrogenated, i.e. with rising boiling points, the advantage of the more favorable energy balance increases. Higher aldehydes having more than 7 carbon atoms are accordingly preferably hydrogenated in the liquid phase.

Hydrogenation in the liquid phase, however, has the disadvantage that, due to the high concentrations both of aldehydes and of alcohols, the formation of high boilers by further reactions and side reactions is promoted. Thus, aldehydes can more easily enter into aldol reactions (addition and/or condensation) and form hemiacetals or full acetals with alcohols. The acetals formed can eliminate water or alcohol to form enol ethers, which are hydrogenated under the reaction conditions to give the saturated ethers. These secondary by-products thus reduce the yield. The by-products referred to high boilers can at best partly be redissociated in downstream plants to products of value, such as starting aldehydes and target alcohols.

Industrial aldehyde mixtures which are used for hydrogenation therefore frequently already contain high boilers in different concentrations.

The hydrogenation of saturated aldehydes (hydroformylates) with addition of water is described, for example, in documents U.S. Pat. No. 5,059,710, U.S. Pat. No. 4,401,384, GB2142010, U.S. Pat. No. 2,809,220, DE19842370A1 and DE10062448A1.

These processes are only of limited suitability for the hydrogenation of decenals to decanols, since the presence of water results in redissociation of at least some of the decanals to one or more $C_5$-aldehyde(s).

Compared to the hydrogenation of saturated aldehydes, the hydrogenation of unsaturated aldehydes to saturated alcohols is much more complex, since not only the carbonyl group but also the olefinic double bond has to be hydrogenated in this case.

A generic process for hydrogenation of saturated or $\alpha,\beta$-unsaturated aldehydes to the corresponding saturated aldehydes is disclosed in DE102007041380A1. The hydrogenation catalyst used therein is a supported catalyst which, as well as the active copper and nickel components, and chromium as a promoter, additionally contains barium oxide.

In the hydrogenation of decenals to decanols over the catalysts comprising barium oxide described in DE102007041380A1 in a long-term test, it was found that decenals are present in the hydrogenation output after more than 1000 hours of operating time.

Decenals in the decanol mixture can be disadvantageous in the further processing thereof. For example, in the production of plasticizers from the decanol mixture, reaction of the decenals can give rise to a product with elevated color number, such that a workup of increased complexity is necessary to lower the color number.

For this reason, it is desirable to provide a decanol mixture which is very substantially free of decenals. Since decenals and decanols, however, have a similar boiling point, physical separation of unconverted decenals out of the decanol mixture is uneconomic.

It is therefore an object of the invention to specify a process of the type specified at the outset, in which, even after long operating times, decenals can be hydrogenated to decanols with high yields. More particularly, the content of unconverted decenals in the hydrogenation output should be less than 1500 ppm, preferably less than 1000 ppm and most preferably less than 600 ppm.

This object is achieved by effecting the hydrogenation in two stages, namely in a first stage in a manner known per se over a catalyst comprising copper, nickel and optionally chromium and/or barium oxide, and subsequently in a second stage with another catalyst which must be free of copper, chromium and nickel.

The invention therefore provides a process for preparing at least one decanol by hydrogenation of at least one decenal, in which a first hydrogenation is effected in the liquid phase over a solid first catalyst, said first catalyst comprising copper and nickel, comprising a second hydrogenation, following the first hydrogenation, in the liquid phase over a solid second catalyst, said second catalyst being free of copper, chromium and nickel.

The process according to the invention, compared to a process which uses only one catalyst, has the following advantages: for the same overall catalyst volume, with comparable yields, a product with a lower content of olefinic compounds is obtained. The consequence of this is that, while complying with a limit of olefinic compounds in the hydrogenation output, a lower specific catalyst volume is needed. Due to the lower catalyst costs and lower frequency of catalyst exchange and associated cost and inconvenience, lower specific hydrogenation costs arise. In addition, shutdown times in production resulting from catalyst exchange are reduced.

Feedstocks for the process according to the invention are decenals ($\alpha,\beta$-unsaturated $C_{10}$-aldehydes). More particularly, $\alpha,\beta$-unsaturated $C_{10}$-aldehydes which have been obtained by aldol condensation of $C_5$-aldehydes are used, for example 2-propylhept-2-enal from n-pentanal and 2-methyl- 2-isopropylhex-2-enal from 3-methylbutanal, or a mixture of isomeric decenals which are obtained by condensation of at least two different $C_5$-aldehydes, for example 4-methyl-2-propylhexanal from cross-aldolization of n-pentanal with 2-methylbutanal. Particular preference is given to hydrogenating decenal mixtures having a content of 2-propylhept-2-enal of more than 85% by mass by the process according to the invention.

A process for preparing such mixtures of $C_5$-aldehydes is described, for example, in DE102009001594A1.

In the process according to the invention, for the first hydrogenation stage, a supported catalyst comprising the hydrogenation-active metals copper, chromium and nickel, and also barium oxide, may be used. Such catalysts are described in DE102007041380A1. The support material may be titanium dioxide, zirconium dioxide, aluminum oxide, silicon dioxide, or the mixed oxides thereof. A preferred support is aluminum oxide, preferably γ-aluminum oxide with BET surface areas between 90 and 200 $m^2/g$. A (first) catalyst usable for the first hydrogenation stage of the process according to the invention contains 1 to 20% by mass of copper, 0.2 to 6% by mass of chromium, 1 to 20% by mass of nickel, in each case calculated as the metal, and 0.1 to 2% by mass of barium, calculated as barium oxide.

In a preferred embodiment, the supported catalyst for the first hydrogenation stage of the process according to the invention contains only copper and nickel as hydrogenation-active metals, i.e. is free of chromium. A preferred support used is aluminum oxide, preferably γ-aluminum oxide with BET surface areas between 90 and 200 $m^2/g$. The catalysts mentioned generally contain 1 to 20% by mass of copper and 1 to 20% by mass of nickel, in each case calculated as the metal, especially 6 to 12% by mass of copper and 3 to 8% by mass of nickel.

It has been found that, surprisingly, in the inventive two-stage hydrogenation, the first catalyst may even be free of barium oxide, without significant formation of acetals.

Thus, the catalyst to be used in the first hydrogenation stage in the process according to the invention is especially a catalyst composed of copper and nickel as hydrogenation-active metals on a support, i.e. without addition of chromium and/or barium oxide.

For the second hydrogenation stage of the process according to the invention, preference is given to using catalysts which comprise palladium or ruthenium as the hydrogenation-active metal.

The hydrogenation catalysts used for the second stage of the process according to the invention may be known supported ruthenium catalysts which contain typically 0.1 to 10% by mass of ruthenium. For example, it is possible to use catalysts whose preparations are described in DE10054347A1 and DE10232868A1.

In the process according to the invention, preference is given to using supported ruthenium catalysts containing 0.5 to 3% by mass of Ru on high-surface area aluminum oxides as the support.

Particular preference is given to palladium catalysts, since the valuable palladium can be recycled better from the spent catalyst.

Suitable palladium catalysts used may be Pd-containing supported catalysts containing 0.1 to 3% by mass of palladium. In the process according to the invention, preference is given to using supported catalysts containing 0.5 to 1.5% by mass of Pd on high-surface area aluminum oxides as the support. Preference is given to using γ-aluminum oxides with a BET surface area between 80 and 180 $m^2/g$ and a pore volume between 0.5 and 0.7 $cm^3/g$.

The catalysts are appropriately used in a form which offers a low flow resistance, for example in the form of granules, pellets or shaped bodies, such as tablets, cylinders, balls, extrudates or rings. They are appropriately activated before use by heating in a hydrogen stream, for example to from 140 to 250° C., if they are not reduced in the hydrogenation reactor. For example, a process for reducing a catalyst with hydrogen in the presence of a liquid phase is described in DE19933348A1.

The proportion by volume of the first catalyst in the overall catalyst volume is preferably 70 to 98%; more particularly, the volume of the first catalyst is at least three times as large as the volume of the second catalyst. Most preferably, the proportion by volume of the first catalyst in the total catalyst volume is 80 to 95%, most preferably 90 to 95%.

In a very particularly preferred embodiment of the process according to the invention, a catalyst composed merely of copper and nickel on a support, i.e. free of chromium and/or barium oxide, is used in the first hydrogenation stage, and a Pd-containing supported catalyst in the second hydrogenation stage. This catalyst combination achieves particularly good hydrogenation results in the process according to the invention, i.e. the proportion of the decenals can be lowered to a particularly high degree, with simultaneously good recyclability of the catalysts, which leads to a particularly economically viable process overall.

In the process according to the invention, the hydrogenation of the decenal mixtures to the corresponding saturated $C_{10}$-alcohols is performed over two catalysts arranged in different reactors or beds. Optionally, the two hydrogenation stages can be effected successively in one reactor. This means that the different catalysts are arranged in different beds in one reactor. In the simplest embodiment, the process according to the invention is performed in a reactor having two beds, one bed being formed by the first catalyst and the other bed being formed by the second catalyst.

In the process according to the invention, preference is given to process versions with at least two reactors, where the second reactor may have one or two beds.

The process according to the invention is preferably performed in at least two reactors connected in series, the first reactor containing the first catalyst and the second reactor containing the second catalyst, and the first hydrogenation being effected in the first reactor and the second hydrogenation being effected in the second reactor.

For each reaction zone of the process according to the invention, it is possible to select different process variants. It can be performed adiabatically, or virtually isothermally, i.e. with a temperature rise less than 10° C., in one or more stages. In the latter case, it is possible for all reactors, appropriately tubular reactors, to be operated adiabatically or virtually isothermally, and also for one or more to be operated adiabatically and the others to be operated virtually isothermally.

The two reaction zones of the process according to the invention are performed preferably continuously and preferably in the trickle phase or in the liquid phase in triphasic reactors in cocurrent, the hydrogen being finely distributed in the liquid aldehyde stream in a manner known per se. In the interests of homogeneous liquid distribution, improved removal of heat of reaction and a high space-time yield, the reactors are preferably operated with high liquid space velocities of 15 to 120 $m^3$ and especially of 25 to 80 $m^3$ per $m^2$ of cross section of the empty reactor and hour. When a reactor is operated isothermally and in straight pass, the specific catalyst space velocity (LHSV=liquid hourly space velocity) may assume values between 0.1 and 10 V.

A specific version of the process according to the invention is characterized in that the first reactor containing the first catalyst is operated in loop mode (external recycling) and the second reactor, which contains either only the second catalyst or the first catalyst in the upper reaction zone and the second catalyst in the lower reaction zone, is operated in straight pass.

Optionally, the hydrogenation can also be performed in three reactors connected in series. In this case, the first reactor containing a portion of the first catalyst is preferably operated in loop mode (external recycling), and the second reactor containing the rest of the first catalyst and the third reactor containing the second catalyst are operated in straight pass. In this case, the first hydrogenation is effected in the first and second reactors and the second hydrogenation is effected in the third reactor.

To minimize side reactions and thus increase the yield, it is appropriate to limit the aldehyde concentration in the reactor feed. More particularly, the proportion of decenal in the feed of the first reactor is between 1 and 35% by mass, preferably between 5 and 25% by mass. The desired concentration range in reactors which are operated in loop mode can be established through the circulation rate (ratio of hydrogenation output recycled to reactant).

The two or more stages of the process according to the invention are performed within a pressure range from 0.5 to 10 MPa, especially between 0.5 and 4 MPa, very particularly in the range from 1 to 2.5 MPa. The hydrogenation temperatures are between 120 and 220° C., especially between 140 and 190° C. The individual stages are operated at the same pressure or different pressures. The temperatures in the individual stages are the same or different.

The hydrogen used for the hydrogenation may comprise inert gases, for example methane or nitrogen. Preference is given to using hydrogen with a purity greater than 98%, especially greater than 99%.

Each reactor can be operated with fresh hydrogen. However, it is also possible that the off gas of one reactor may entirely or partially be the feed hydrogen for another reactor. In the latter case, liquid hydrogenation material (reactant/products) and hydrogen can flow through the reactors in the same or reverse sequence.

The hydrogenation product is worked up by distillation. This is done at standard pressure or preferably under reduced pressure. The hydrogenation mixture is preferably separated into three fractions, namely first runnings, decanol fraction (saturated $C_{10}$-alcohols) and high boiler fraction (substances with higher boiling points than the decanols) separated. When the first runnings still contain $C_{10}$-aldehydes, they can be recycled partly into the hydrogenation.

The $C_{10}$-alcohols are, as already mentioned, preferably used for the production of plasticizers or detergents.

The examples which follow are intended to illustrate the invention without restricting the scope of application which is evident from the description and the claims.

EXAMPLE 1

Noninventive

Hydrogenation with First Catalyst (Cu/Cr/Ni on $Al_2O_3$ Support)

A reaction output from the continuous aldolization of n-pentanal and 2-methylbutanal containing about 88% by mass of 2-propylheptenal and about 3.2% by mass of 4-methyl-2-propylhexenal was hydrogenated continuously in the liquid phase in a circulation apparatus at 180° C. and 25 bar absolute over 105.3 g (corresponding to 150 ml) of a Cu/Cr/Ni catalyst on $Al_2O_3$ support (extrudates: diameter 1.5 mm, length 3-5 mm) containing 6% by mass of copper, 3.1% by mass of nickel and 0.6% by mass of chromium. The throughput was 0.10 l/h of reactant, corresponding to an LHSV of 0.66 $h^{-1}$, at a circulation rate of 40 l/h. The offgas rate was 60 l (STP)/h. The reactant and product analyses in % by mass are reproduced in Table 1.

TABLE 1

Hydrogenation of $C_{10}$-aldehydes over the Cu/Cr/Ni catalyst

| | Time/h | | | |
|---|---|---|---|---|
| | 0 | 500 | 1000 | 3000 |
| 2-Methylbutanal | 2.48 | 0.03 | 0.05 | 0.04 |
| n-Pentanal | 2.98 | 0.03 | 0.05 | 0.04 |
| 2-Methylbutanol | 0.01 | 2.92 | 2.76 | 2.96 |
| n-Pentanol | 0.09 | 3.70 | 3.44 | 3.71 |
| Intermediate runnings* | 0.01 | 1.03 | 1.19 | 1.21 |
| 4-Methyl-2-propylhexenal | 3.20 | 0.03 | 0.05 | 0.04 |
| 2-Propylheptanal | 0.00 | 0.25 | 0.44 | 0.69 |
| 4-Methyl-2-propylhexanal | 0.00 | 0.03 | 0.05 | 0.06 |
| 4-Methyl-2-propylhexanol | 0.00 | 3.14 | 3.15 | 3.11 |
| 4-Methyl-2-propylhexenol | 0.00 | 0.01 | 0.01 | 0.01 |
| 2-Propylheptenal | 87.99 | 0.35 | 0.47 | 0.85 |
| 2-Propylheptanol | 0.00 | 86.55 | 85.89 | 85.20 |
| 2-Propylheptenol | 0.01 | 0.01 | 0.03 | 0.09 |
| High boilers | 1.68 | 1.43 | 1.53 | 1.41 |
| Residue/GC | 1.56 | 0.73 | 0.89 | 0.58 |

*Intermediate runnings (including $C_5$ esters and $C_5$ acids)

As can be inferred from Table 1, the two unsaturated $C_{10}$ aldehydes 2-propylheptenal and 4-methyl-2-propylhexenal were converted over the Cu/Cr/Ni standard catalyst with high selectivity to the products of value 2-propylheptanol and 4-methyl-2-propylhexanol.

The unconverted $C_5$-aldehydes present in the reactant (n-pentanal and 2-methylbutanal) were converted virtually completely to corresponding $C_5$-alcohols. The residual contents of unsaturated $C_{10}$-aldehyde, 2-propylheptenal, rose from 0.35% by weight on commencement of the hydrogenation after 500 hours to about 0.85% by weight after 3000 hours of the experiment. In the product spectrum of the hydrogenation over the Cu/Cr/Ni catalyst, the intermediate of the 2-propylheptenal hydrogenation, the saturated $C_{10}$-aldehyde 2-propylheptanal, was detected.

EXAMPLE 2

Noninventive

Hydrogenation with First Catalyst (Cu/Ni on $Al_2O_3$ Support)

A reaction output from the continuous aldolization of n-pentanal and 2-methylbutanal containing about 86.5% by mass of 2-propylheptenal and 3.3% by mass of 4-methyl-2-propylhexenal was hydrogenated continuously in the liquid phase in a circulation apparatus at 180° C. and 25 bar absolute over 109.8 g (corresponding to 150 ml) of a Cu/Ni catalyst on $Al_2O_3$ support (same support as in Example 1) containing 9.5% by mass of copper and 6.1% by mass of nickel. The throughput was 0.10 l/h of reactant, corresponding to an LHSV of 0.66 $h^{-1}$, at a circulation rate of 40 l/h. The offgas rate was 60 l (STP)/h. The reactant and product analyses in % by mass are reproduced in Table 2.

TABLE 2

Hydrogenation of $C_{10}$-aldehydes over the Cu/Ni catalyst

| | Time/h | | | |
|---|---|---|---|---|
| | 0 | 500 | 1000 | 3000 |
| 2-Methylbutanal | 2.89 | 0.03 | 0.03 | 0.02 |
| n-Pentanal | 4.03 | 0.04 | 0.04 | 0.04 |
| 2-Methylbutanol | 0.02 | 2.99 | 2.99 | 2.98 |
| n-Pentanol | 0.14 | 4.65 | 4.75 | 4.80 |
| Intermediate runnings* | 0.01 | 1.35 | 1.34 | 1.32 |
| 4-Methyl-2-propylhexenal | 3.30 | 0.01 | 0.00 | 0.01 |
| 2-Propylheptanal | 0.14 | 0.01 | 0.01 | 0.01 |
| 4-Methyl-2-propylhexanal | 0.00 | 0.09 | 0.06 | 0.05 |
| 4-Methyl-2-propylhexanol | 0.00 | 2.91 | 2.90 | 2.90 |
| 4-Methyl-2-propylhexenol | 0.00 | 0.01 | 0.01 | 0.01 |
| 2-Propylheptenal | 86.67 | 0.19 | 0.34 | 0.65 |
| 2-Propylheptanol | 0.05 | 85.54 | 85.46 | 85.10 |
| 2-Propylheptenol | 0.01 | 0.00 | 0.00 | 0.02 |
| High boilers | 1.72 | 1.43 | 1.44 | 1.54 |
| Residue/GC | 1.03 | 0.76 | 0.63 | 0.55 |

*Intermediate runnings (including $C_5$ esters and $C_5$ acids)

Under the selected reaction conditions, the residual contents of unsaturated $C_{10}$-aldehyde, 2-propylheptenal, of 0.19% by weight after 500 hours rose to about 0.65% by weight after 3000 hours of the experiment. This result is comparable to the hydrogenation result in Example 1.

In contrast to Cu/Cr/Ni catalyst (Example 1), the intermediate of the 2-propylheptenal hydrogenation, the saturated $C_{10}$-aldehyde 2-propylheptanal, is converted virtually completely to the 2-propylheptanol product of value over the Cu/Ni catalyst with much higher Cu and Ni contents.

EXAMPLE 3

Inventive

Hydrogenation with a Combination of Cu/Cr/Ni Catalyst and Ru Catalyst

The example which follows shows the results of the hydrogenation according to the present invention. Instead of one catalyst, the catalyst bed consisted of a combination of two catalysts. The total catalyst volume as in Example 1 was 150 ml.

The main proportion of the catalyst bed, at 120 ml, was the Cu/Cr/Ni catalyst which was also used in Example 1. This catalyst was positioned on the inflow side of the reactor.

The Cu/Cr/Ni catalyst (extrudates: diameter 1.5 mm, length 3-5 mm) was followed by a supported ruthenium catalyst (1.5% by mass of Ru on γ-aluminum oxide as the support) with catalyst volume 30 ml.

For the hydrogenation, reactant of the same composition as in Example 1 was used.

The reaction conditions of the hydrogenation at 180° C., 25 bar and a reactant throughput of 0.10 l/h with a circulation rate of 40 l/h were comparable to conditions of the hydrogenation in Example 1.

The results of the hydrogenation over the inventive catalyst combination are shown in Table 3.

TABLE 3

Hydrogenation over Cu/Cr/Ni and Ru catalyst combination

| | Time/h | | | |
|---|---|---|---|---|
| | 0 | 500 | 1000 | 3000 |
| 2-Methylbutanal | 2.48 | 0.03 | 0.05 | 0.05 |
| n-Pentanal | 2.98 | 0.03 | 0.05 | 0.04 |
| 2-Methylbutanol | 0.01 | 2.98 | 2.77 | 2.98 |
| n-Pentanol | 0.09 | 3.70 | 3.54 | 3.71 |
| Intermediate runnings* | 0.01 | 1.17 | 1.22 | 1.21 |
| 4-Methyl-2-propylhexenal | 3.20 | 0.03 | 0.07 | 0.01 |
| 2-Propylheptanal | 0.00 | 0.64 | 0.82 | 1.39 |
| 4-Methyl-2-propylhexanal | 0.00 | 0.08 | 0.08 | 0.05 |
| 4-Methyl-2-propylhexanol | 0.00 | 3.15 | 3.21 | 3.11 |
| 4-Methyl-2-propylhexenol | 0.00 | 0.01 | 0.01 | 0.01 |
| 2-Propylheptenal | 87.99 | 0.03 | 0.04 | 0.07 |
| 2-Propylheptanol | 0.00 | 86.56 | 85.93 | 85.21 |
| 2-Propylheptenol | 0.01 | 0.01 | 0.03 | 0.09 |
| High boilers | 1.68 | 1.49 | 1.42 | 1.41 |
| Residue/GC | 1.56 | 0.72 | 0.76 | 0.58 |

*Intermediate runnings (including $C_5$ esters and $C_5$ acids)

The results in Table 3 show that the yields of the 2-propylheptenal hydrogenation in the presence of the inventive catalyst combination are comparable with the yields achievable over the standard catalyst in Example 1.

According to the present analysis of the reaction outputs, the contents of desired 2-propylheptanol product of value (2-PH-ol) in both cases are between 85 and 86% by mass.

In contrast to the standard method with one catalyst in Example 1 with rising contents of unsaturated $C_{10}$-aldehyde 2-propylheptenal, the 2-propylheptenal contents in the reaction output were distinctly reduced in the case of use of the catalyst combination.

After an experiment time of about 3000 hours, a low content of 2-propylheptenal of about 0.07% by mass, corresponding to 700 ppm, was determined. According to the present results, the 2-propylheptenal was preferentially converted to 2-propylheptanal.

EXAMPLE 4

Inventive

Hydrogenation with a Combination of Cu/Ni Catalyst and Pd Catalyst

The example which follows shows the results of the hydrogenation according to the present invention using a second catalyst combination which consisted of a Cu/Ni catalyst as the first catalyst and a downstream palladium catalyst. As in Example 2, the total catalyst volume was 150 ml.

Maintaining the same volume ratio as in Example 3, the reactor was filled from the inflow side with 120 ml of the Cu/Ni catalyst and with 30 ml of the palladium catalyst (0.5% by mass of Pd) in the same geometric shape (extrudates: diameter 1.5 mm, length 2 to 4 mm).

For the hydrogenation, reactant of the same composition as in Example 2 was used. The hydrogenation was effected under the same reaction conditions as in the preceding examples, i.e. at 180° C., 25 bar and $C_g$-aldehyde throughput 100 ml/h.

The results of the hydrogenation over the second inventive catalyst combination are shown in Table 4.

TABLE 4

Hydrogenation over Cu/Ni and Pd catalyst combination

| | Time/h | | | |
|---|---|---|---|---|
| | 0 | 500 | 1000 | 3000 |
| 2-Methylbutanal | 2.89 | 0.03 | 0.03 | 0.02 |
| n-Pentanal | 4.03 | 0.04 | 0.04 | 0.04 |
| 2-Methylbutanol | 0.02 | 2.99 | 2.99 | 2.98 |
| n-Pentanol | 0.14 | 4.68 | 4.79 | 4.86 |
| Intermediate runnings* | 0.01 | 1.35 | 1.34 | 1.32 |
| 4-Methyl-2-propylhexenal | 3.30 | 0.01 | 0.00 | 0.01 |
| 2-Propylheptanal | 0.14 | 0.18 | 0.22 | 0.41 |
| 4-Methyl-2-propylhexanal | 0.00 | 0.08 | 0.07 | 0.05 |
| 4-Methyl-2-propylhexanol | 0.00 | 2.91 | 2.90 | 2.91 |
| 4-Methyl-2-propylhexenol | 0.00 | 0.01 | 0.01 | 0.01 |
| 2-Propylheptenal | 86.67 | 0.01 | 0.02 | 0.04 |
| 2-Propylheptanol | 0.05 | 85.54 | 85.48 | 85.25 |
| 2-Propylheptenol | 0.01 | 0.00 | 0.00 | 0.00 |
| High boilers | 1.72 | 1.43 | 1.47 | 1.52 |
| Residue/GC | 1.03 | 0.74 | 0.63 | 0.58 |

As can be inferred from Table 4, comparable yields were achieved in the hydrogenation of unsaturated $C_{10}$-aldehydes in the presence of Cu/Ni and Pd catalyst combination to those in the case of use of the Cu/Ni catalyst system in Example 2.

Compared to Example 2 with one catalyst, the residual contents of $C_{10}$-aldehyde 2-propylheptenal in the product output were distinctly reduced by the downstream Pd catalyst. After about 3000 hours of the experiment, a 2-propylheptenal content of about 400 ppm was determined.

The invention claimed is:

1. A process for preparing a decanol, the process comprising:
   (a) hydrogenating at least one decenal in a liquid phase over a solid first catalyst, comprising copper and nickel to form a resulting mixture; and then,
   (b) hydrogenating the resulting mixture in the liquid phase over a solid second catalyst, which is free of copper, chromium and nickel.

2. The process of claim 1, wherein the second catalyst comprises palladium.

3. The process of claim 1, wherein the second catalyst comprises ruthenium.

4. The process of claim 1, wherein a proportion by volume of the first catalyst in a total catalyst volume is 70 to 98 %.

5. The process of claim 4, wherein the volume of the first catalyst is at least three times the volume of the second catalyst.

6. The process of claim 1, wherein:
   the hydrogenating (a) and (b) occur in at least two reactors connected in series;
   a first reactor comprises the first catalyst and a second reactor comprises the second catalyst;
   the hydrogenating (a) occurs in the first reactor and the hydrogenating (b) occurs in the second reactor.

7. The process of claim 6, wherein:
   the hydrogenating (a) and (b) occur in three reactors connected in series;
   the first reactor comprises a portion of the first catalyst and is operated in loop mode;
   the second reactor comprises a remainder of the first catalyst;
   the third reactor comprises the second catalyst;
   the hydrogenating (a) occurs in both the first reactor and the second reactor; and
   the hydrogenating (b) occurs in the third reactor.

8. The process of claim 1, wherein the hydrogenating (a) and (b) occur in a reactor having two beds, such that a first bed comprises the first catalyst and a second bed comprises the second catalyst.

9. The process of claim 1, wherein the first catalyst is free of barium oxide.

10. The process of claim 1, wherein the first catalyst is free of chromium.

* * * * *